US 8,114,066 B2

(12) United States Patent
Naef et al.

(10) Patent No.: US 8,114,066 B2
(45) Date of Patent: Feb. 14, 2012

(54) DISPLAY FOR AN INFUSION DELIVERY SYSTEM

(75) Inventors: Gregor Naef, Niederrohrdorf (CH); Pia Bertapelle, Long Island City, NY (US)

(73) Assignee: Roche Diagnostics International AG, Steinhausen (CH)

( * ) Notice: Subject to any disclaimer, the term of this patent is extended or adjusted under 35 U.S.C. 154(b) by 0 days.

(21) Appl. No.: 12/940,123

(22) Filed: Nov. 5, 2010

(65) Prior Publication Data
US 2011/0112478 A1    May 12, 2011

Related U.S. Application Data

(63) Continuation of application No. PCT/EP2009/003247, filed on May 6, 2009.

(60) Provisional application No. 61/051,111, filed on May 7, 2008.

(51) Int. Cl.
*A61K 9/22* (2006.01)
(52) U.S. Cl. .................................... 604/890.1
(58) Field of Classification Search ......... 604/131–155, 604/246–256, 890.1
See application file for complete search history.

(56) References Cited

U.S. PATENT DOCUMENTS

| | | | |
|---|---|---|---|
| 5,984,894 A | | 11/1999 | Poulsen et al. |
| 6,551,276 B1 * | | 4/2003 | Mann et al. .................. 604/131 |
| 7,018,361 B2 * | | 3/2006 | Gillespie et al. ............. 604/151 |
| 7,717,903 B2 * | | 5/2010 | Estes et al. ................. 604/890.1 |
| 2006/0106345 A1 * | | 5/2006 | Flaker et al. ................. 604/131 |
| 2006/0142692 A1 * | | 6/2006 | Jacobson et al. .............. 604/67 |
| 2006/0184123 A1 * | | 8/2006 | Gillespie et al. ............. 604/155 |
| 2007/0073236 A1 | | 3/2007 | Mernoe et al. |
| 2007/0087725 A1 * | | 4/2007 | Anderson ................... 455/348 |
| 2007/0165020 A1 | | 7/2007 | Haueter et al. |
| 2008/0252798 A1 * | | 10/2008 | Vitito ......................... 348/837 |
| 2009/0069749 A1 * | | 3/2009 | Miller et al. ................. 604/151 |
| 2009/0128307 A1 * | | 5/2009 | Hentsch et al. ............. 340/425.5 |
| 2010/0161220 A1 * | | 6/2010 | Masuda et al. .............. 701/208 |
| 2010/0294877 A1 * | | 11/2010 | Jianu .............................. 244/2 |

FOREIGN PATENT DOCUMENTS

| WO | 2006/032653 A2 | 3/2006 |
|---|---|---|
| WO | 2007/033010 A1 | 3/2007 |

OTHER PUBLICATIONS

International Search Report, Application No. PCT/EP2009/003247, Oct. 19, 2009, 10 pages.

* cited by examiner

*Primary Examiner* — Tan-Uyen T. Ho
*Assistant Examiner* — Victoria P Campbell
(74) *Attorney, Agent, or Firm* — Dinsmore & Shohl LLP

(57) ABSTRACT

The present disclosure generally relates to an infusion pump for dispensing medication. More specifically, the present disclosure relates to a display unit that can be pulled out by a user.

11 Claims, 4 Drawing Sheets

DISPLAY FOR AN INFUSION DELIVERY SYSTEM

CROSS REFERENCE TO RELATED APPLICATIONS

The present application claims the benefit of U.S. Provisional Application No. 61/051,111, filed May 7, 2008, which is incorporated herein by reference in its entirety. This application is a continuation of application PCT/EP2009/003247, filed May 6, 2009.

TECHNICAL FIELD

The present disclosure generally relates to an infusion pump for dispensing medication. More specifically, it relates to a display for a portable infusion system such as an insulin pump.

BACKGROUND

Medical devices that pump medication into an individual are used in the medical industry. Typically, the medication that is delivered from such medical devices depends on the medical condition to be treated. For example, it is increasingly common to deliver insulin using an insulin pump to treat a patient.

Conventionally, these infusion systems have housing with a display for relevant information. For example, for an insulin pump, it is common to display information such as the basal rate, the life of the battery, time, date and so forth. However, these displays, together with other components such as a cartridge, determine the size of the overall housing of an infusion pump. However, it is becoming more common to make these infusion systems smaller so that they can be discretely used. This reduces the display area so that relevant information has to be displayed in a relatively smaller space, which may be difficult to read for certain users. Such devices although may give be advantageous for discreet use are not the best when used by an elderly person or a person with poor eyesight since they can not effectively read the information displayed in the screen.

Infusion pumps have emerged that have no display and need to be operated wirelessly by a separate device such as a remote controller. However such devices may not be for users who would like to see some information on the pump and do not want to carry a separate device to operate the pump. In addition, the display unit is unprotected and, therefore, prone to environmental contaminants, scratching, or breaking. This typically requires a user to have an additional carrying case that covers the display. Again, such carrying cases are not convenient if the user wants to look at the information on the display, because the infusion pump will have to be removed from the carrying case.

Therefore, in the medical industry, it is challenging and difficult to have an infusion pump that is small, lightweight and that can be discreetly used while not reducing the display area. Additionally, in the medical industry, it is also challenging and difficult to have an infusion pump where the display is not prone to environmental contaminants, but can be easily accessible and discreetly used.

SUMMARY

It is against the above background that the various embodiments of the present invention provide certain unobvious advantages and advancements over the prior art.

In accordance with one embodiment, an infusion system for pumping fluid into a body of a user is disclosed. The infusion system may have an infusion pump with a housing that includes a slidable panel and a non-slidable panel, wherein the non-slidable panel includes an opening, a release mechanism, and a display that can be pulled out of the opening upon activation of the release mechanism. The display is designed to provide information to the user regarding the use of the infusion system.

These and other features and advantages of the present invention will be more fully understood from the following detailed description of the invention taken together with the accompanying claims. It is noted that the scope of the claims is definitely by the recitations therein and not by the specific discussion of the features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

Skilled artisans appreciate that elements in the figures are illustrated for simplicity and clarity and have not necessarily been drawn to scale. For example, the dimensions of some of the elements in the figure may be exaggerated relative to other elements to help improve understanding of the embodiment(s) of the present invention.

DETAILED DESCRIPTION

The following description of the preferred embodiment is merely exemplary in nature and is in no way intended to limit the invention or its application or uses.

Figure 1:
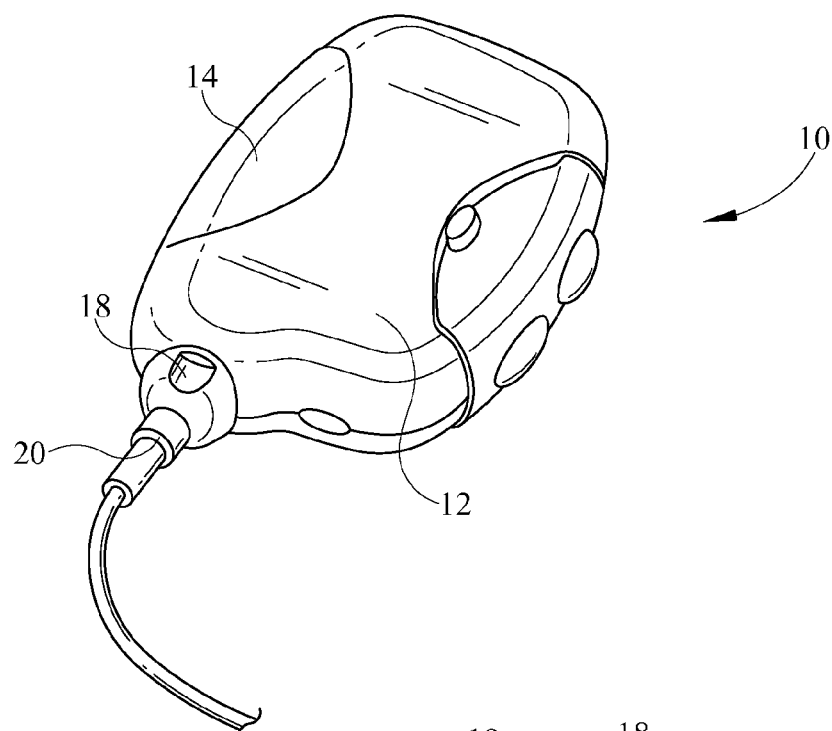
FIG. 1 is a perspective view of the infusion delivery system in accordance with an embodiment of the present invention.
Figure 2:
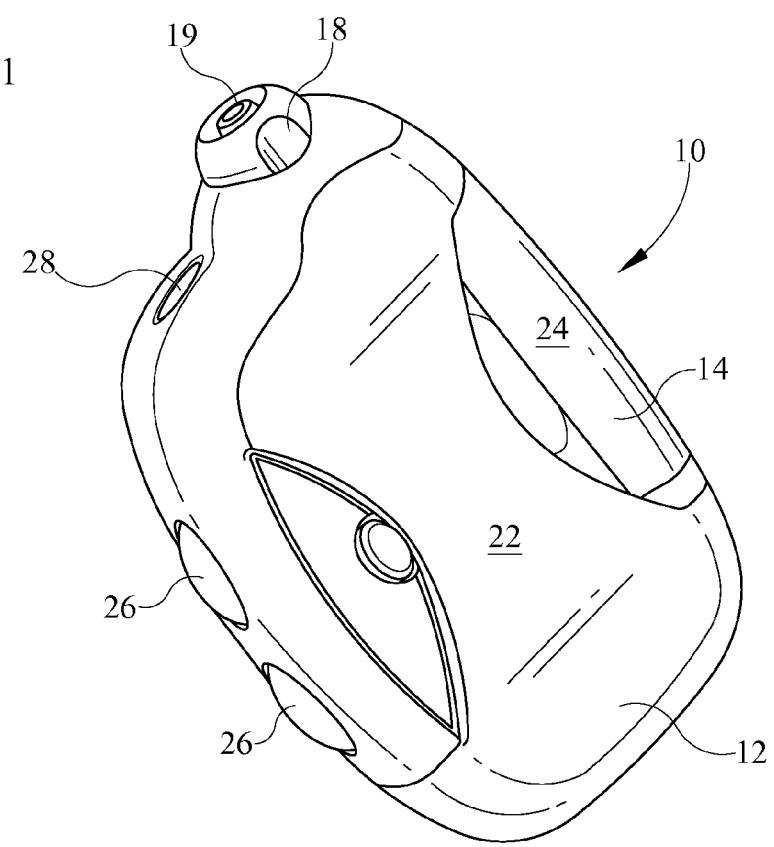
FIG. 2 is a perspective view of the infusion delivery system without the infusion set of FIG. 1.
Figure 7:
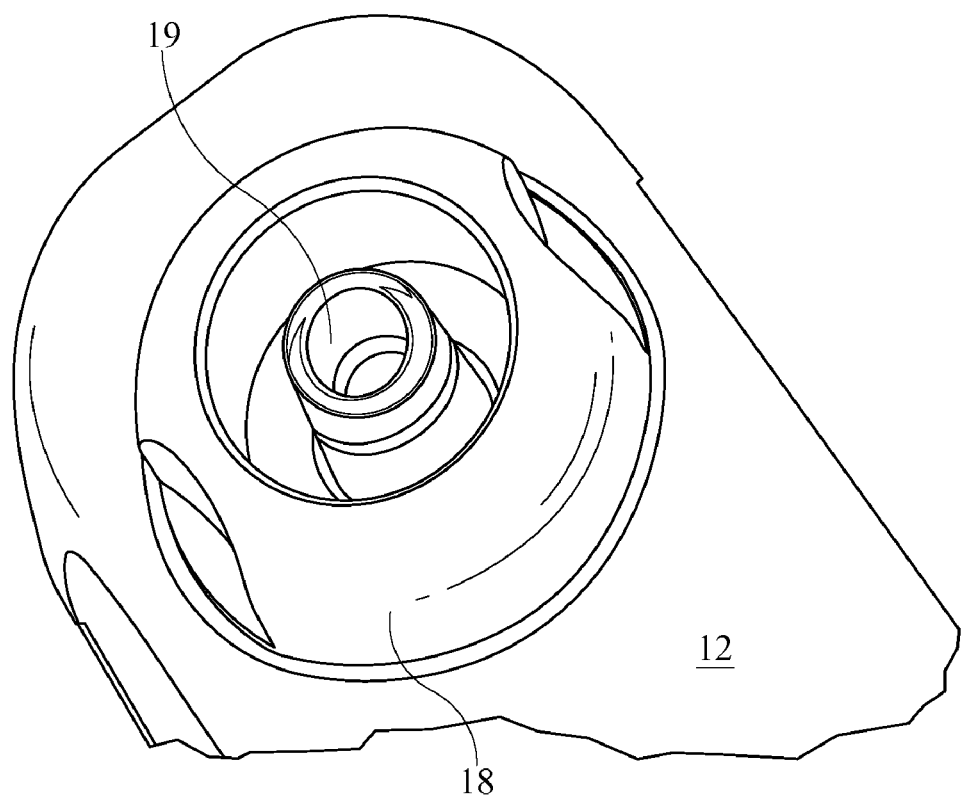
FIG. 7 is a top view of the cap and the luer connection of the infusion delivery system of FIG. 1.

Referring in particular to FIGS. 1 and 2, an infusion delivery system is generally represented by reference numeral 10. As can be seen in the drawing, the infusion delivery system 10 comprises an infusion housing 12, a fluid storing means 14 such as a cartridge, a cap 18 to hold the fluid storing means 14 in place and an infusion set 20 that is connected to the fluid cartridge through the cap 18. One end of the infusion set 20 is inserted into the user and the other end is inserted into the cap 18, thereby creating a fluidic path from the fluid storing means 14 to the user through the infusion set 20. Although an insulin pump is shown, it must be understood that this embodiment of the invention is not limited to insulin pumps but to any pump that can be used to deliver medication. As shown in FIG. 7, the infusion set 20 may be connected to the cap 18 through a luer connection 19.

The housing 12 of the infusion delivery system 10 is made of plastic or any eco-friendly material. The shape of the housing is such that it is ergonomically designed for handling ease and discreet use. As shown in FIG. 1, the housing 12 comprises an opaque portion 22 and a transparent portion 24. In one embodiment, the transparent portion 24 is positioned such that the fluid storing means 14 is visible to the user of the infusion delivery system 10. In another embodiment, the entire housing may be made of an opaque or a transparent material.

Referring to FIG. 2, the housing 12 comprises at least one control or button 26 to control the infusion of medication from fluid storing means 14. The control 26 may also be used to scroll through information on the display screen as will be explained in detail. The housing 12 also includes an optical port 28 such as an LED that may be used to give visual indication of selected information. For example, the optical port 28 may change color if the power level falls below a pre-determined level. Alternatively, the optical port may be used to indicate the fluid level in the fluid storing means 14.

Figure 3:
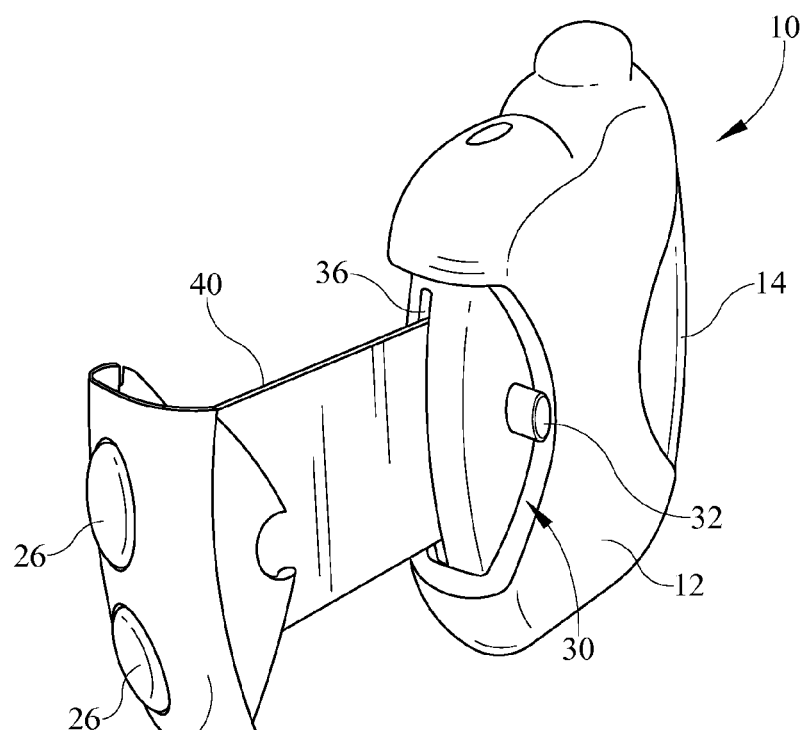
FIG. 3 is a perspective view of the infusion delivery system with the display unit in an exposed position.
Figure 4:
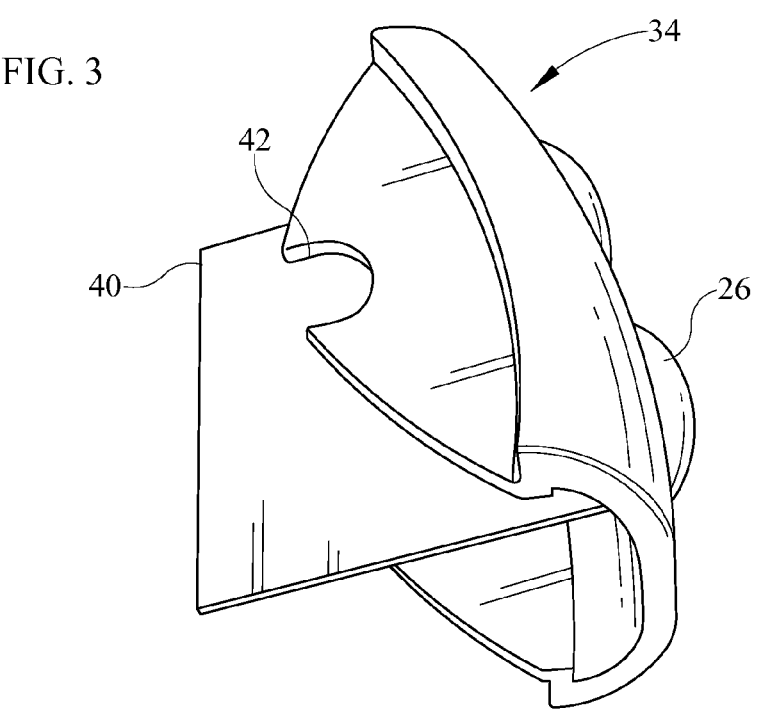
FIG. 4 is a close up view of the housing and the display unit of FIG. 3.
Figure 5:
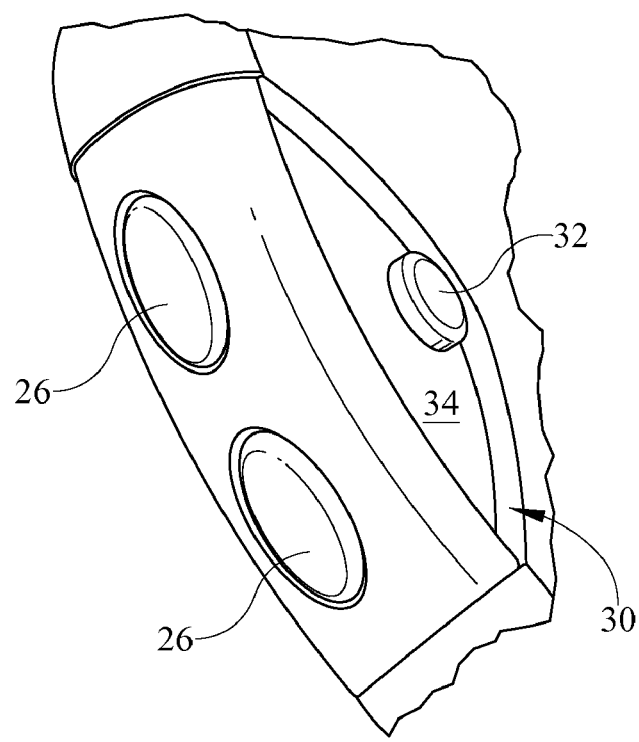
FIG. 5 is a close up view of the slidable panel with controls of FIG. 4.

Referring in particular to FIGS. 3, 4 and 5, the housing 12 further includes a cutout portion generally shown by reference numeral 30. The cutout portion 30 includes a release mechanism 32, a slidable panel 34 and a slot/opening 36 to house a display unit 40. In operation, when the release mechanism 32 is pressed, the slidable panel 34 slides outward and away from the housing 12, thereby releasing the display unit 40 from the slot 36. The display unit 40 in this position is held between the slidable panel 34 and the opening 36. As shown in the drawing, specifically in FIG. 4, the control 26 is part of the slidable panel 34 such that they also move away from the housing 12 when the release mechanism 32 is pressed. In another embodiment, the at least one control 26 may be positioned on the housing 12 so as to not include the slidable panel 34. In order to push the display unit 40 back to the opening 36, the user presses on the slidable panel 34 such that groove 42 on the slidable panel 34 locks with the release mechanism 32. Although not shown in the drawings, it may be understood that a mechanism can be provided on the slidable panel 34 such that the retraction of the display unit 40 into the opening 36 takes place in one action.

In yet another embodiment, the slidable panel is the release mechanism such that upon pressing of the slidable panel the display slides out of the opening.

In another embodiment (not shown), the display unit 40 is capable of displaying relevant information regarding the use of the infusion device. For example, the information displayed may be the basal rate profile, history of bolus, the different bolus profiles, and so forth. The display unit may be an LCD screen or a flat screen. Other technologies that are typically used to display device information may be used in still other embodiments. In addition, the display may be coupled to the at least one control 26 such that information may be scrolled.

As can be seen from the description, an infusion pump with a pull out display unit 40 has several advantages. Firstly, it is possible to make a small and lightweight pump without compromising the display space. In addition, since the display unit 40 is not open to the environment, it is less prone to contamination, scratching and breakage. In addition, a user can easily access relevant information by pulling out the display unit at the press of a button.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modification and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. An infusion system for pumping fluid into a body of a user, the system comprising:
 a housing, wherein the housing includes a slidable panel comprising a groove and a non-slidable panel, wherein the non-slidable panel includes an opening;
 a release mechanism; and
 a display unit comprising a first surface coupled to the slidable panel and a second surface slidingly engaged with the opening, wherein the display unit slides transversely along and out of the opening upon activation of the release mechanism and when the display unit is in a closed position, the groove of the slideable panel partially surrounds the release mechanism such that the release mechanism is accessible.

2. The system of claim 1, wherein upon activation of the release mechanism, the slidable panel moves away from the non-slidable panel.

3. The system of claim 2, wherein the display is held in place between the slidable panel and the opening.

4. The system of claim 1, wherein the release mechanism is a button.

5. The system of claim 1, wherein the release mechanism comprises at least one control.

6. The system of claim 1, wherein the slidable panel is the release mechanism such that upon pressing of the slidable panel the display slides out of the opening.

7. The system of claim 1, wherein the display unit is capable of conveying information regarding the infusion system.

8. The system of claim 1, wherein the display unit is a LCD screen or a touch screen.

9. An infusion system for pumping fluid into a body of a user, the system comprising:
 a housing comprising a cutout portion;
 an opening formed in the cutout portion of the housing;
 a display slidingly engaged with the opening;
 a slidable panel fixedly engaged with the display unit; and
 a release mechanism disposed on the cutout portion of the housing that releases the display unit from a closed position to allow a transition to an open position, wherein:
 when the display unit is in the closed position, the opening and the slidable panel cooperate to form a surround that envelops the display unit, the slidable panel overlaps the cutout portion of the housing, and the slideable panel partially surrounds the release mechanism such that the release mechanism is accessible; and
 when the display unit is in the open position, the display unit is located between the slideable panel and the cutout portion of the housing.

10. The system of claim 9, wherein the slidable panel comprises a rounded inner surface, and the rounded inner surface of the slidable panel is engaged with the display unit.

11. The system of claim 10, the rounded inner surface of the slidable panel partially encloses the display unit.

* * * * *

UNITED STATES PATENT AND TRADEMARK OFFICE
CERTIFICATE OF CORRECTION

| | |
|---|---|
| PATENT NO. | : 8,114,066 B2 |
| APPLICATION NO. | : 12/940123 |
| DATED | : February 14, 2012 |
| INVENTOR(S) | : Gregor Naef et al. |

It is certified that error appears in the above-identified patent and that said Letters Patent is hereby corrected as shown below:

Col. 1, Line 37, "although may give be" should read --although may be--

Col. 1, Line 39, "they can not" should read --they cannot--

Figure 6:
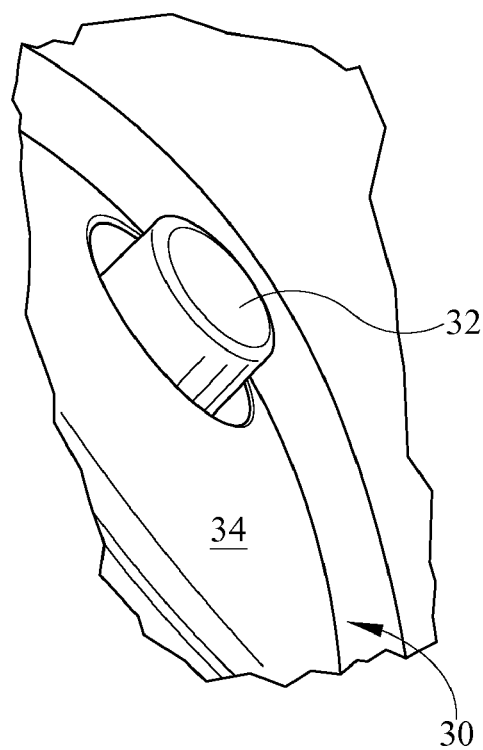
FIG. 6 is top view of the release mechanism.

Col. 2, Line 30, "FIG 6 is top view" should read --FIG 6 is a top view--

Signed and Sealed this
Tenth Day of July, 2012

David J. Kappos
*Director of the United States Patent and Trademark Office*